(12) United States Patent
Strobl

(10) Patent No.: US 10,682,536 B1
(45) Date of Patent: Jun. 16, 2020

(54) MULTI-STAGE NASAL FILTER

(71) Applicant: Frederick Thomas Strobl, Scottsdale, AZ (US)

(72) Inventor: Frederick Thomas Strobl, Scottsdale, AZ (US)

( * ) Notice: Subject to any disclaimer, the term of this patent is extended or adjusted under 35 U.S.C. 154(b) by 0 days.

(21) Appl. No.: 16/703,707

(22) Filed: Dec. 4, 2019

Related U.S. Application Data

(60) Provisional application No. 62/873,209, filed on Jul. 12, 2019.

(51) Int. Cl.
| | |
|---|---|
| *A62B 23/06* | (2006.01) |
| *A61M 16/10* | (2006.01) |
| *A61M 16/00* | (2006.01) |
| *A61M 15/08* | (2006.01) |
| *A61K 33/18* | (2006.01) |

(52) U.S. Cl.
CPC .............. *A62B 23/06* (2013.01); *A61M 15/08* (2013.01); *A61M 15/085* (2014.02); *A61M 16/0093* (2014.02); *A61M 16/1055* (2013.01); *A61K 33/18* (2013.01)

(58) Field of Classification Search
CPC . A62B 23/06; A61M 16/009; A61M 16/1055; A61M 15/08; A61M 15/085; A61K 33/18
See application file for complete search history.

(56) References Cited

U.S. PATENT DOCUMENTS

| | | | | |
|---|---|---|---|---|
| 3,457,917 | A | * 7/1969 | Mercurio | A62B 23/06 128/204.12 |
| 3,463,149 | A | 8/1969 | Albu | |
| 5,417,205 | A | * 5/1995 | Wang | A62B 23/06 128/204.12 |
| 5,568,808 | A | * 10/1996 | Rimkus | A62B 23/06 128/204.12 |
| 6,119,690 | A | * 9/2000 | Pantaleo | A62B 23/06 128/206.11 |
| 6,494,205 | B1 | * 12/2002 | Brown | A61M 15/08 128/204.12 |
| 7,918,224 | B2 | 4/2011 | Dolezal | |
| 10,322,304 | B2 | 5/2019 | Kronenberg | |
| 2005/0066972 | A1 | * 3/2005 | Michaels | A62B 23/06 128/206.11 |
| 2018/0304108 | A1 | * 10/2018 | Curtis | A62B 23/06 |

* cited by examiner

*Primary Examiner* — Bradley H Philips
*Assistant Examiner* — Vincent D Hoang
(74) *Attorney, Agent, or Firm* — Jennings Strouss & Salmon PLC; Michael K. Kelly; Daniel R. Pote

(57) ABSTRACT

Devices and methods of inhibiting the inhalation of particulates using a resiliently deformable filter packaged in a sealed envelope containing a liquid medium. The method includes opening the sealed package to thereby expose the filter to ambient air; removing the filter from the package; inserting the filter into a distal region of a nostril; and urging the filter from the distal region to a proximal region of the nostril while simultaneously swabbing the distal region with the liquid disinfectant. The filter includes: an initial stage characterized by a first pore size; an intermediate stage characterized by a second pore size; and a final stage characterized by a third pore size, wherein the third pore size is a smaller than the first and second pore sizes.

3 Claims, 3 Drawing Sheets

MULTI-STAGE NASAL FILTER

PRIORITY CLAIM

This non-provisional application claims priority to provisional application Ser. No. 62/873,209 filed Jul. 12, 2019, the entire contents of which are hereby incorporated by this reference.

TECHNICAL FIELD

The present disclosure generally relates to filtration devices insertable into human nostrils for removing particulates from inhaled ambient air. More particularly, the disclosure relates to multi-stage devices configured to trap successively smaller particles.

BACKGROUND OF THE DISCLOSURE

Prior art nasal filters designed to be removably inserted into the nostrils offer various filter materials exhibiting a range of porosities.

Albu U.S. Pat. No. 3,463,149 discloses a filter plug comprising a cotton body contained within a fabric covering. A medicament containing cylinder, having a stationary ported piston received therein, dispenses medicament into the body upon relative movement of the cylinder and piston.

Kronenberg U.S. Pat. No. 10,322,304 B2 discloses a two-stage filter system including a microfiber filter and a nanofiber filter used in series, with the nanofiber filter located downstream of the microfiber filter.

Dolezal U.S. Pat. No. 7,918,224 B2 discloses a pair of ellipsoidal filters exhibiting a corrugated structure to increase the surface area available for filtration.

The entire contents of the foregoing Albu, Kronenberg, and Dolezal patents are hereby incorporated herein.

Presently known nasal filters are unsatisfactory in that they allow some portion of the inhaled air stream to bypass the seal formed between the outer perimeter of the filter and the internal nasal surfaces. In addition, very small particle sizes often pass through the filter and enter the body, potentially causing infection.

Nasal filter devices and systems are thus needed which overcome these and other shortcomings of the prior art.

SUMMARY OF THE DISCLOSURE

Various embodiments of the present disclosure relate to single and multi-stage nasal filters. A preferred embodiment comprises a pair of three stage filters connected by a band (e.g., 0.25—1 mm cross-section) to facilitate manual removal, where the initial (first) stage has a smaller pore size than the intermediate (second) stage, and the final (third) stage has a smaller pore size than the first and second stages. One or more stages may be electrostatic and/or coated (or saturated) with an antiseptic or disinfectant such as povidone iodine or iodoprovidone, commonly marketed under the brand name Betadine™ or silver.

The shape and size of the second and third stages may be configured to induce venturi-type turbulence proximate the stage 2/stage 3 interface, causing increased contact between particulates and the antiseptic borne by the filter fibers. For example, eddy currents resulting from turbulent air flow may cause pathogens to contact (and thus killed by) antiseptic borne by one or more of:

i) the distal surface of the second stage filter;
ii) the proximal surface of the second stage filter;
iii) internal passages within the second stage filter;
iv) the distal surface of the third stage filter;
v) the proximal surface of the third stage filter;
vi) internal passages within the third stage filter;
vii) aerosolized antiseptic proximate the distal surface of the second stage filter;
viii) aerosolized antiseptic proximate the proximal surface of the second stage filter;
ix) aerosolized antiseptic proximate the distal surface of the third stage filter;
x) aerosolized antiseptic proximate the proximal surface of the third stage filter; and/or
xi) aerosolized antiseptic within the space between the second and third stage filters.

In an embodiment, the second stage comprises a resiliently deformable foam-type material having slightly larger cross-section than the nasal passage within which it is disposed. The third stage comprises a sheet or blanket of fabric loosely enveloping the second stage and forming an air gap therebetween. Once the assembly is inserted into the nostril, the second stage resiliently expands to synchronously urge both the second and third stages against the internal surfaces of the septum and nares, forming a perimeter seal. In this way, as the "oversized" assembly is inserted into the distal portion of the nasal passage, the exposed mucosa is swabbed with antiseptic. This swabbing effectively kills any pathogenic particulates which might otherwise enter the body through the distal mucosa located "upstream" of the inserted filter assembly.

A further embodiment contemplates a sealed package (e.g., plastic, foil) which contains a single or multi-stage nasal filter immersed in an aqueous antiseptic environment. The sealed package maintains sterility of the device prior to insertion, and also ensures that the filter materials (e.g., cotton, foam, fabric) remain saturated with antiseptic solution until used. This also ensures that the distal mucosa will be liberally swabbed during insertion, without the need for supplemental swabbing.

BRIEF DESCRIPTION OF THE DRAWING FIGURES

A more complete understanding of the embodiments of the present disclosure may be derived by referring to the detailed description and claims when considered in connection with the following illustrative figures, and:

It will be appreciated that elements in the figures are illustrated for simplicity and clarity and have not necessarily been drawn to scale. For example, the dimensions of some of the elements in the figures may be exaggerated relative to other elements to enhance clarity of the accompanying descriptions of various illustrated embodiments. Moreover, although various embodiments are illustrated in the context of a single device to be inserted into a single nostril, those skilled in the art will appreciate that each single filter assembly comprises one of a pair of identical or mirror image filters configured to be inserted into both nostrils.

DETAILED DESCRIPTION OF EXEMPLARY EMBODIMENTS

Figure 1:
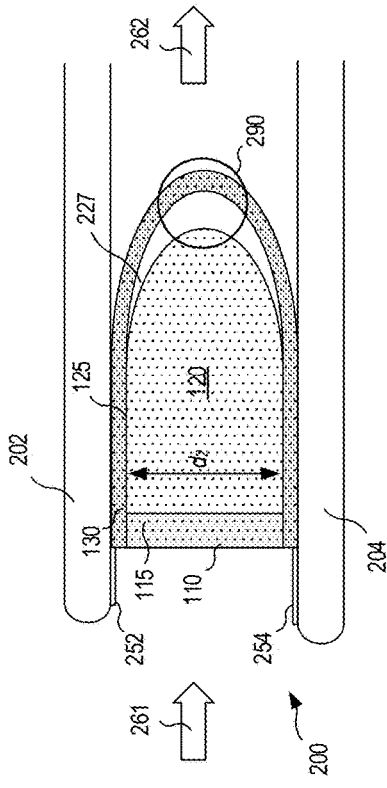
FIG. 1 is a schematic cross-section view of a multi-stage filter prior to nasal insertion in accordance with various embodiments.
Figure 2:
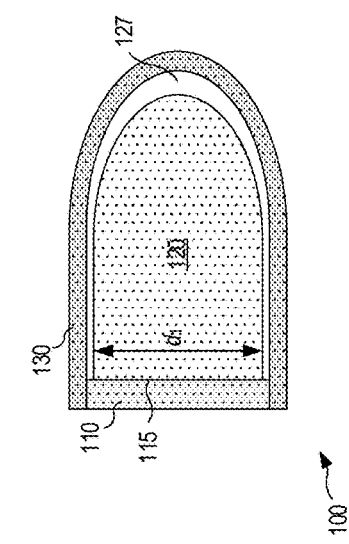
FIG. 2 is a schematic cross-section view of the multi-stage filter subsequent to nasal insertion in accordance with various embodiments.
Figure 3:
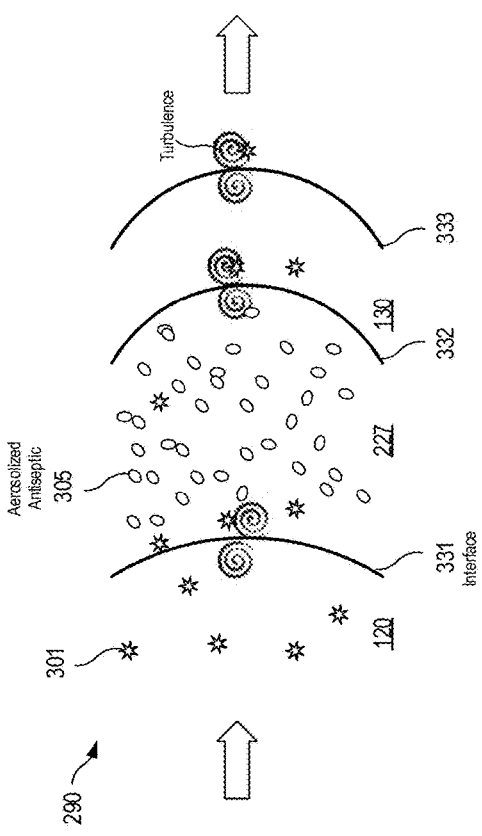
FIG. 3 is a detail schematic cross-section view of venturi-type turbulence proximate stages 2 and 3 in accordance various embodiments.
Figure 4:
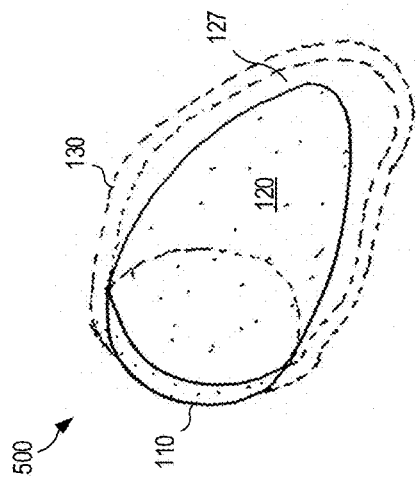
FIG. 4 is a schematic cross-section view of an alternate embodiment of a multi-stage filter in accordance with various embodiments.
Figure 5:
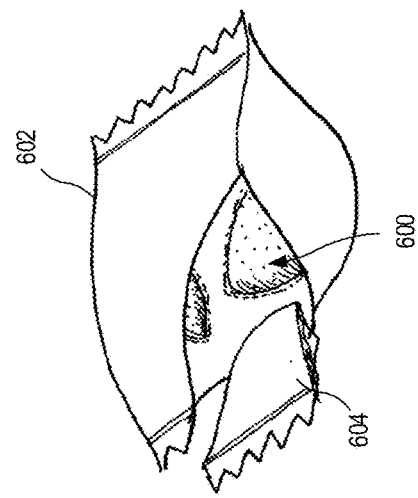
FIG. 5 is a schematic perspective view of a one side of a dual multi-stage nasal filter in accordance with various embodiments.
Figure 6A:
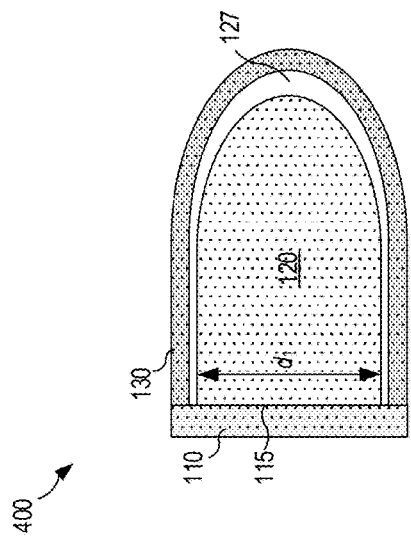
FIG. 6A is a perspective view of a sealed package containing a nasal filter saturated in an aqueous antiseptic solution in accordance with various embodiments.
Figure 6B:
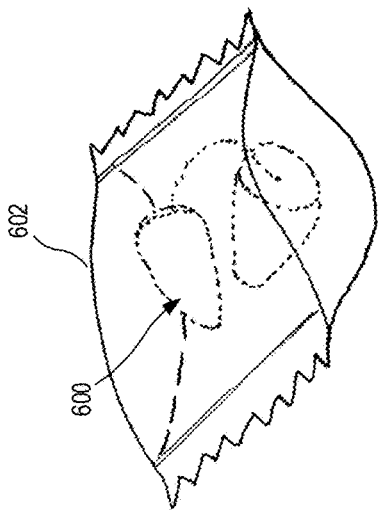
FIG. 6B is a perspective view of the package of FIG. 6A torn open to reveal the saturated nasal filter in accordance with various embodiments.
Figure 7:
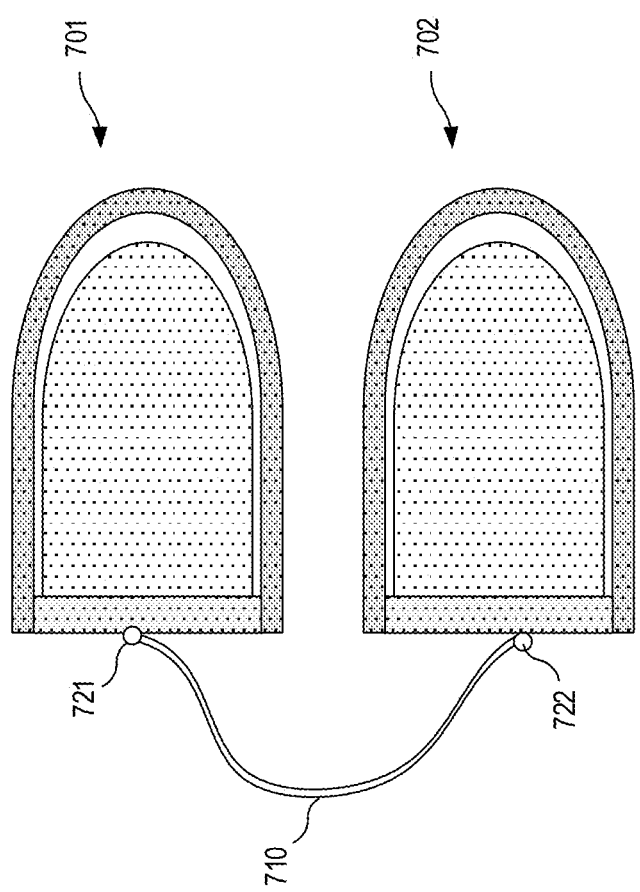
FIG. 7 is a cross section view of a pair of filters interconnected by a band.

Referring now to FIG. 1, a first embodiment of a multi-stage nasal filter assembly 100 comprises a first stage filter 110, a second stage filter 120, and a third stage filter 130. The first stage filter 110 may comprise a conventional plastic, nylon, semi rigid, or resiliently deformable circumference supporting a fabric or other filter material. The interface 115 between the first and second stages may comprise a bearing surface, contactless (a gap), or partial contact between the first and second stages. An air gap 127 between the second and third stages provides a region in which antiseptic liberated from one or more filters may be aerosolized due to turbulent air flow, as described in greater detail below in conjunction with FIG. 3.

With continued reference to FIG. 1, second stage filter 120 may be generally cone shaped with a domed terminus, while also exhibiting a generally elliptical cross section to closely mate with the internal nasal cavity upon insertion therein. Prior to insertion, the foam or other resiliently deformable material comprising the second stage filter exhibits a cross-section dimension $d_1$. As described below in connection with FIG. 2, as the device is inserted into and manually positioned slightly upwardly into the nostril 200, the second stage filter material compress slightly, and thereafter expands in situ to urge the third stage material radially outwardly against the internal nasal cavity, forming a perimeter seal. (See the interface 125 between the second and third stage filters shown in FIG. 2.)

FIG. 2 shows the filter assembly inserted into the nostril between the septum 202 and the nares 204, with the direction of inhaled air flow being indicated by arrows 261 (pre-filter) and 262 (post filter). As shown, the compressed cross-section dimension $d_2$ is slightly less than the uncompressed dimension $d_1$ of FIG. 1. As the antiseptic saturated filter material is inserted, the exposed distal mucosa 252 and 254 are swabbed, providing an antiseptic coating which eliminates (or at least mitigates) the entry vector for pathogens associated with prior art devices. An air gap 290 between the second and third stages is discussed below in connection with FIG. 3.

FIG. 3 schematically illustrates turbulent air flow resulting from venturi-type effects of air flowing through a restricted zone (e.g., the second and/or third stage filters). As shown, an air gap 227 may be formed between the distal surface 331, of the first stage filter and the proximal surface 332 of the third stage filter. In particular, pathogens 301 intermingle with aerosolized droplets 305 in the air gap 227 between the second and third stages, as well as in the region 120 upstream of the second filter, the regions within third stage filter 130 and downstream of the second filter stage, and/or near the proximal surface 333 of the third stage filter.

FIG. 4 is a schematic cross-section view of an alternate embodiment of a multi-stage filter 400 wherein the outer perimeters of the first stage 110 and the third stage 130 are substantially coextensive proximate their junction.

FIG. 5 is a schematic perspective view of one side 500 of a dual multi-stage nasal filter showing the air gap 127 in three dimensions. In this regard, note that one or more air gaps for facilitating eddy currents and turbulence may be configured to exhibit any desired size or volume.

FIG. 6A is a perspective view of a sealed package 602 containing a pair 600 of nasal filters saturated in an aqueous antiseptic solution in accordance with various embodiments.

FIG. 6B is a perspective view of the package of FIG. 6A shown torn open by removing segment 604 to reveal the saturated nasal filters.

FIG. 7 illustrates a pair of nasal filters 701, 702 and a band 710 interconnecting the two filters together. In the illustrated embodiment the band 701 is connected to filter 701 at a connection point 721, and the band 701 is connected to filter 702 at a connection point 722. Those skilled in the art will appreciate that the band may connect to each filter at any convenient point on any desired filter stage.

In various embodiments, pore sizes for the materials comprising the filter stages range from 0.001 microns to 1000 microns. Moreover, a particular filter stage may include multiple pore sizes (which may increase turbulence).

Additional embodiments may contemplate a filter wherein a particular stage itself comprises two "stages," wherein the airflow is forced sideways along the inspiration path causing increased interaction with filter walls.

A further embodiment involves a single stage device for allergens, wherein the single stage comprises a compressible foam or other resiliently deformable material with entrained antiseptic.

A method is thus provided for impeding the inhalation of particulates using a resiliently deformable filter packaged in a sealed envelope containing a liquid medium. The method includes: opening the sealed package to thereby expose the filter to ambient air; removing the filter from the package; inserting the filter into a distal region of a nostril; and urging the filter from the distal region to a proximal region of the nostril while simultaneously swabbing the distal region with liquid medium present on the perimeter of the filter.

In an embodiment, the filter is characterized by a mean pore size in the range of 0.1 to 100 micrometers (um), and preferably 0.5 to 50 um, and most preferably 0.1 to 10 um.

In an embodiment, the particulates comprise allergens, and further wherein the filter is characterized by a mean pore size in the range of 3 to 7 um.

In an embodiment, the liquid medium comprises an antiseptic.

In an embodiment, the liquid medium comprises a disinfectant.

In an embodiment, the particulates comprise microorganisms.

In an embodiment, the particulates comprise allergens.

In an embodiment, the filter comprises electrostatic material.

In an embodiment, the liquid medium comprises povidone iodine.

In an embodiment, swabbing comprises rotating the filter within the distal region of the nostril.

In an embodiment, swabbing comprises simultaneously rotating and urging the filter upwardly within the nostril.

In an embodiment, the method further includes: leaving the filter within the proximal region for a period of time in the range of five minutes to eighteen hours; and thereafter removing the filter from the nostril.

In an embodiment, the method further includes: leaving the filter within the proximal region for a period of time in the range of one to six hours; and thereafter removing the filter from the nostril.

In an embodiment, the filter further comprises a pair of filters connected by a band.

In an embodiment, the method further includes removing the pair of filters from respective nostrils by manually pulling on the band.

In an embodiment, the filter further includes: an initial stage characterized by a first pore size; an intermediate stage characterized by a second pore size; and a final stage characterized by a third pore size; wherein the third pore size is a smaller than the first and second pore sizes.

A nasal filter is provided for insertion into a nostril having an internal nostril circumference. The filter includes: an initial stage characterized by a first pore size; an intermediate stage characterized by a second pore size; and a final stage characterized by a third pore size; wherein the third pore size is a smaller than the first and second pore sizes.

In an embodiment, the initial stage comprises a perimeter ring supporting a substantially planar filter material; the intermediate stage comprises a resiliently deformable filter material having a substantially flat distal end adjacent the initial stage and a dome shaped proximal end; and the final stage comprises a sheet of fabric loosely enveloping the intermediate stage and forming an air gap therebetween.

In an embodiment, at least one of the initial, intermediate, and final stages comprise an antiseptic coating.

In an embodiment, the resiliently deformable filter material is configured to urge the sheet of fabric against internal nostril circumference The description of exemplary embodiments of various filter stages and their materials and functions is merely exemplary and is intended for purposes of illustration only; the following description is not intended to limit the scope of the disclosure or the claims. Moreover, recitation of multiple embodiments having stated features, compositions, or properties is not intended to exclude other embodiments having additional features, compositions, or properties, or other embodiments incorporating different combinations of the stated features, compositions, or properties, unless otherwise noted herein.

Although exemplary embodiments of the present disclosure are set forth herein, it should be appreciated that the disclosure is not so limited. For example, although materials, media, apparatus, systems, and methods are described in connection with multi-stage filters, the invention may also be used in the context of single stage filters. Various modifications, variations, and enhancements of the materials, methods, and media set forth herein may be made without departing from the spirit and scope of this disclosure.

The invention claimed is:

1. A nasal filter for insertion into a nostril having an internal nostril circumference, the filter comprising:
    an initial stage characterized by a first pore size;
    an intermediate stage characterized by a second pore size; and
    a final stage characterized by a third pore size;
    wherein;
the initial stage comprises a perimeter ring supporting a substantially planar filter material; the intermediate stage comprises a resiliently deformable filter material having a substantially flat distal end adjacent the initial stage and a dome shaped proximal end; and the final stage comprises a sheet of fabric loosely enveloping the intermediate stage and forming an air gap therebetween; and the third pore size is a smaller than the first and second pore sizes.

2. The filter of claim 1, wherein at least one of the initial, intermediate, and final stages comprise an antiseptic coating.

3. The filter of claim 2, wherein:
    the resiliently deformable filter material is configured to urge the sheet of fabric against internal nostril circumference.

\* \* \* \* \*